United States Patent
Sankaran et al.

(10) Patent No.: US 12,394,528 B2
(45) Date of Patent: *Aug. 19, 2025

(54) SYSTEMS AND METHODS FOR SIMULATION OF OCCLUDED ARTERIES AND OPTIMIZATION OF OCCLUSION-BASED TREATMENTS

(71) Applicant: HeartFlow, Inc., Redwood City, CA (US)

(72) Inventors: Sethuraman Sankaran, Palo Alto, CA (US); Leo J. Grady, Darien, CT (US); Charles A. Taylor, Atherton, CA (US); Christopher K. Zarins, Austin, TX (US)

(73) Assignee: Heartflow, Inc., Mountain View, CA (US)

( * ) Notice: Subject to any disclaimer, the term of this patent is extended or adjusted under 35 U.S.C. 154(b) by 1155 days.

This patent is subject to a terminal disclaimer.

(21) Appl. No.: 17/237,144

(22) Filed: Apr. 22, 2021

(65) Prior Publication Data

US 2021/0241920 A1    Aug. 5, 2021

Related U.S. Application Data

(63) Continuation of application No. 15/421,832, filed on Feb. 1, 2017, now Pat. No. 11,017,904, which is a continuation of application No. 14/598,050, filed on Jan. 15, 2015, now Pat. No. 9,594,876.

(60) Provisional application No. 62/074,693, filed on Nov. 4, 2014.

(51) Int. Cl.
G16H 50/50    (2018.01)
G06F 17/18    (2006.01)
G16H 20/40    (2018.01)
G16H 40/67    (2018.01)
G16Z 99/00    (2019.01)

(52) U.S. Cl.
CPC ............ *G16H 50/50* (2018.01); *G06F 17/18* (2013.01); *G16H 20/40* (2018.01); *G16H 40/67* (2018.01); *G16Z 99/00* (2019.02)

(58) Field of Classification Search
None
See application file for complete search history.

(56) References Cited

U.S. PATENT DOCUMENTS

| | | | |
|---|---|---|---|
| 8,315,812 B2 | 11/2012 | Taylor | |
| 2012/0041318 A1 | 2/2012 | Taylor | |
| 2013/0197884 A1 | 8/2013 | Mansi et al. | |
| 2014/0073976 A1 | 3/2014 | Fonte et al. | |
| 2014/0073977 A1 | 3/2014 | Grady et al. | |

FOREIGN PATENT DOCUMENTS

| | | |
|---|---|---|
| JP | 2012217805 A | 11/2012 |
| WO | WO 2013/031744 A1 | 3/2013 |
| WO | WO 2013/071219 A1 | 5/2013 |
| WO | WO 2014/134289 A1 | 9/2014 |

OTHER PUBLICATIONS

Wachowiak et al. (Proceedings of the 19th International Symposium on High Performance Computing Systems and Applications (HPCS '05); IEEE-2005:7 pages).*
International Search Report and Written Opinion for corresponding PCT Application No. PCT/US2015/057743 dated Jan. 28, 2016 (11 pages).
Bok Y. Lee, et al.: "*Noninvasive Hemodynamic Evaluation in Selection of Amputation Level*", Surgery, Gynecology & Obstetrics, Aug. 1979, vol. 149, pp. 241-244.
Robert W. Barnes et al.: "*An Index of Healing in Below-Knee Amputation: Leg blood pressure by Doppler ultrasound*", Surgery, Jan. 1976, vol. 79, No. 1, pp. 13-20.
Bok Y. Lee, MD., "*Hemodynamic Evaluation in Selection of Amputation Level*", State of Effort—Hemodynamic Evaluation Chief, Surgical Service, Veterans Administration Hospital, pp. 85-104.
Wagner, FW, Transcutaneous Doppler ultrasound in the prediction of healing and the selection of surgical level for dysvascular lesions of the toes and forefoot, 1979, vol. 142, pp. 110-114, Clinical Orthopaedics and Related Research.
Caroli et al. (Kidney International (2013) vol. 84:1237-1245; published May 29, 2013).
Pekkan et al. (Med Biol Eng Comput (2008) vol. 46:1139-1152).
Sankaran et al. (Annals of Biomedical Engineering (2012) vol. 40:2228-2242).
Antiga et al. (Med. Biol. Eng. Comput. (2008) vol. 46:1097-1112).
Bode et al. (PLoS One (2012) vol. 7:e34491, 1-8).
Huberts (Personalized Computational Modeling of Vascular Access Creation; Thesis for Technische Universiteit Eindhoven (2012); printed by Proefschriftmaken.nl; pp. 1-226).
Taylor et al. (Computer Methods in Applied Mechanics and Engineering (1998) vol. 158:155-196).
Taylor et al. (Annu. Rev. Biomed. Eng. (2009) vol. 11:109-134).
Zangan and Falk (Semin Intervent Radiol (2009) vol. 26:144-150).

* cited by examiner

*Primary Examiner* — Lori A. Clow
(74) *Attorney, Agent, or Firm* — Bookoff McAndrews, PLLC

(57) ABSTRACT

Systems and methods are disclosed for simulation of occluded arteries and/or optimization of occlusion-based treatments. One method includes obtaining a patient-specific anatomic model of a patient's vasculature; obtaining an initial computational model of blood flow through the patient's vasculature based on the patient-specific anatomic model; obtaining a post-treatment computational model by modifying portions of the initial computational model based on an occlusion-based treatment; generating a pre-treatment blood flow characteristic using the initial computational model or computing a post-treatment blood flow using the post-treatment computational model; and outputting a representation of the pre-treatment blood flow characteristic or the post-treatment blood flow characteristic.

20 Claims, 9 Drawing Sheets

SYSTEMS AND METHODS FOR SIMULATION OF OCCLUDED ARTERIES AND OPTIMIZATION OF OCCLUSION-BASED TREATMENTS

RELATED APPLICATION(S)

This application is a continuation of and claims the benefit of priority to U.S. application Ser. No. 15/421,832, filed Feb. 1, 2017, which is a continuation of U.S. application Ser. No. 14/598,050. (now U.S. Pat. No. 9,594,876), filed Jan. 15, 2015 which claims priority to U.S. Provisional Application No. 62/074,693 filed Nov. 4, 2014, all of which are hereby incorporated herein by reference in their entireties.

FIELD OF THE DISCLOSURE

Various embodiments of the present disclosure relate generally to patient treatment assessment, treatment planning, and related methods. More specifically, particular embodiments of the present disclosure relate to systems and methods for simulation of occluded arteries and optimization of occlusion-based treatments.

BACKGROUND

Occlusive disease may involve a narrowing of arteries that causes a decrease in blood supply to organs and/or muscles (and tissues surrounding the organ and/or muscles). A patient suffering from an occlusive disease may experience pain, numbness, or weakness where there is poor circulation due to the blood vessel narrowing. Prolonged poor circulation may lead to ulcers, acute or chronic ischemia, gangrene, etc. Occlusive diseases may manifest in various ways, including, e.g., atherosclerosis or peripheral vascular disease. In addition, occlusive disease may often be present with other disease, for instance, heart disease.

Occlusion-based treatments may be performed to treat trauma, infection, ischemia, and/or gangrene, and improve the survival rate and quality of life of a patient. Treatments may include external (e.g., surgical) means or internal (e.g., endovascular) means. Specifically, occlusion-based treatments may include altering blood flow by ligating, obstructing, or removing blood vessels. For instance, amputation or surgical removal of organs and/or tumors may be performed where a candidate amputation or extirpation site is identified. Arteries downstream of the chosen site may be removed from blood circulation. Another example of occlusion-based treatment may include embolization therapy, which may involve embolizing organ sites that host cancer cells. Yet another exemplary occlusion-based treatment may include surgical ligation of blood vessels, e.g., during planned, elective, and/or emergency operations.

Such occlusion-based treatments may re-distribute blood flow following the treatment. While the occlusion-based treatments may improve perfusion, the resultant, re-distributed blood flow may not be taken into account when planning a patient's treatment. For example, effects of blood flow redistribution from removal of downstream arteries downstream of organs and/or tumors may not be evaluated prior to amputation or surgical removal of those organs and/or tumors. Embolization therapy may also result in re-distribution of blood flow. Embolization therapy may additionally cause a change in perfusion of various organs upstream or downstream of the chosen embolization site. However, the impact that embolization therapy may have on blood flow may not be evaluated prior to therapy. Changes in blood flow as a result of blood vessel ligation also may not be analyzed prior to the ligation.

Redistributed blood flow from occlusion-based treatments affect hemodynamic parameters associated with the blood flow. However, the impact of occlusion-based treatment on patient-specific hemodynamic parameters may be unknown before treatment. In other words, treatments are being performed without an understanding of the treatment's efficacy in improving perfusion. Thus, a desire exists to improve treatment planning by accounting for the impact that an occlusion-based treatment may have on blood flow.

The foregoing general description and the following detailed description are exemplary and explanatory only and are not restrictive of the disclosure.

SUMMARY

According to certain aspects of the present disclosure, systems and methods are disclosed for simulation of occluded arteries and optimization of occlusion-based treatments.

One method includes: obtaining a patient-specific anatomic model of a patient's vasculature; obtaining an initial computational model of blood flow through the patient's vasculature based on the patient-specific anatomic model; obtaining a post-treatment computational model by modifying portions of the initial computational model based on an occlusion-based treatment; generating a pre-treatment blood flow characteristic using the initial computational model or computing a post-treatment blood flow using the post-treatment computational model; and outputting a representation of the pre-treatment blood flow characteristic or the post-treatment blood flow characteristic.

In accordance with another embodiment, a system for optimizing occlusion-based treatments comprises: a data storage device storing instructions for optimizing occlusion-based treatments; and a processor configured for: obtaining a patient-specific anatomic model of a patient's vasculature; obtaining an initial computational model of blood flow through the patient's vasculature based on the patient-specific anatomic model; obtaining a post-treatment computational model by modifying portions of the initial computational model based on an occlusion-based treatment; generating a pre-treatment blood flow characteristic using the initial computational model or computing a post-treatment blood flow using the post-treatment computational model; and outputting a representation of the pre-treatment blood flow characteristic or the post-treatment blood flow characteristic.

In accordance with another embodiment, a non-transitory computer readable medium for use on a computer system containing computer-executable programming instructions for performing a method of optimizing occlusion-based treatments, the method comprising: obtaining a patient-specific anatomic model of a patient's vasculature; obtaining an initial computational model of blood flow through the patient's vasculature based on the patient-specific anatomic model; obtaining a post-treatment computational model by modifying portions of the initial computational model based on an occlusion-based treatment; generating a pre-treatment blood flow characteristic using the initial computational model or computing a post-treatment blood flow using the post-treatment computational model; and outputting a representation of the pre-treatment blood flow characteristic or the post-treatment blood flow characteristic.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
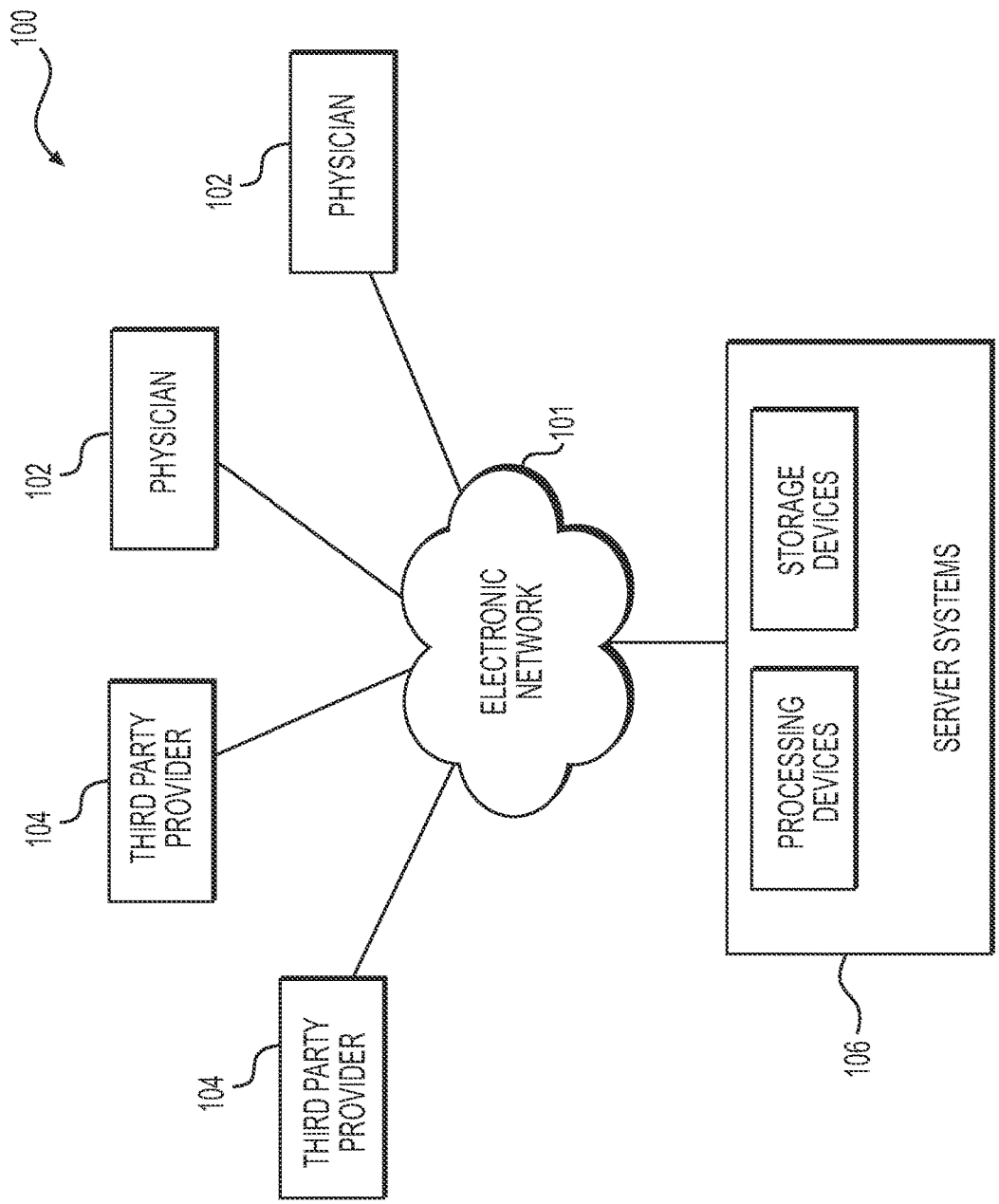
FIG. 1 is a block diagram of an exemplary system and network for simulating occluded arteries and/or optimizing occlusion-based treatments, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

The present disclosure includes systems and methods for optimizing occlusion-based treatment by accounting for the changes in blood flow that may result from treatment. The efficacy of a treatment may be gauged prior to performing the treatment by understanding how a treatment may alter blood flow post-treatment. Furthermore, the present disclosure may provide systems and methods to understand how a treatment may alter blood flow for a particular patient and patient condition. Thus, the present disclosure includes systems and methods for improving the occlusion-based treatment planning process by determining blood flow resulting from treatment and using the determined resultant blood flow to select a treatment (optimally) suitable for a patient condition.

In one embodiment, blood flow simulation(s) may be used to predict the impact of an occlusion-based treatment on blood flow. For example, computational methods may be used to model blood flow simulation, as well as optimize parameters for treatment. The systems and methods included in the present disclosure may also be used to model the impact of progressive occlusive disease (e.g., if a 70% stenosis is present in the renal artery, a system disclosed may be used to model the implications of occlusion of that artery).

In one embodiment, the computational methods for simulating the hemodynamic impact of an occlusion-based treatment may include modeling an arterial system, pre-treatment (e.g., pre-amputation or pre-cancer therapy). For example, the simulation may include, as a threshold step, constructing a computational model of a patient's blood vessels (e.g., based on data from imaging performed on the patient). Blood flow simulations may be performed, for instance, by solving Navier-Stokes equations using a discretized finite element mesh of the computational model and boundary conditions based on organ demand. In one embodiment, the computational model may include machine learning methods (e.g., machine learning methods to estimate hemodynamic characteristics and/or to adaptively improve estimates of hemodynamic characteristics). Furthermore, in one embodiment, organ demand may be calculated based on population-averaged values scaled by patient mass, unless otherwise available. Alternatively, a reduced order model may be used to solve for the hemodynamics and related quantities of interest (e.g., as described in U.S. Pat. No. 8,315,812 filed Jan. 25, 2011, the entire disclosure of which is hereby incorporated by reference in its entirety). The reduced order model may involve solving one-dimensional non-linear or linear equations of blood flow, or computing flow and pressure using a modified Poiseulle's law with non-linear stenosis pressure loss models, along with Bernoulli's equation to account for kinetic energy of blood.

Alternatively or in addition, a machine learning approach may be used to solve for the hemodynamic characteristics of the pre-treatment patient-specific model. In one embodiment, features of the computational model from which effects on hemodynamics are calculated and a regressor (e.g., a regressor computed using a database of 3D simulations) may be used to map the inputs (e.g., the arterial system) to hemodynamic quantities of interest (e.g., as described in U.S. Nonprovisional application Ser. No. 13/895,893 filed May 16, 2013, the entire disclosure of which is hereby incorporated by reference in its entirety).

In one embodiment, a new post-treatment model may be obtained to reflect one or more candidate occlusion-based treatments (e.g., amputation or resection). In one embodiment, obtaining the post-treatment model may include constructing the model reflecting one or more candidate occlusion-based treatments. Alternately or in addition, obtaining the post-treatment model may include modifying an initial anatomical model to represent one or more candidate occlusion-based treatments. Any portion of the method described above may be performed to compute new hemodynamic values. Understanding the hemodynamic impact of an occlusion treatment may provide hypothetical, post-treatment blood pressures and velocities for the imaged patient. By extension, tissue perfusion of organs of interest as well as any other hemodynamic quantity of interest (e.g., blood pressure at specified sites) may be calculated using the post-treatment blood pressure and velocities. For example, the difference between pre-treatment and computed post-treatment tissue perfusion level or other quantities of interest may be output. For example, the output may include transmitting and/or presenting the computed results (e.g., to a physician) for the entire post-treatment model or at regions of interest. Such a presentation may include graphical, pictorial, and/or user-interactive interfaces. Another output may include storing the computed results to an electronic storage medium.

Further, optimal treatment parameters may be calculated. Infeasible parameters of treatment options can be input, e.g., from a database or by a physician. An example of an infeasible parameter may include amputation sites downstream of a proximal location of gangrene. Feasible regions may be based on constraints in the operation theater, e.g., ease of surgery. Preferred treatment parameters may also be prescribed, either automatically (e.g., from a default set of parameters, from a learned association between the patient-specific model and various parameters, etc.) or from user input. A cost function for optimizing occlusion-based treatments may be defined based on a specific type of treatment. Any optimization algorithm may be used to identify optimal treatment parameters. These algorithms may include derivative-free algorithms, where optimal treatment parameters may be obtained by performing repeated simulations until a termination criterion is met. Alternatively, a gradient-based algorithm may be used where derivatives of a cost function with respect to treatment parameters may be calculated, and methods including steepest descent or conjugate gradients may be used to compute optimal parameters.

Referring now to the figures, FIG. 1 depicts a block diagram of an exemplary system 100 and network for simulating occluded arteries and optimizing occlusion-based treatments, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
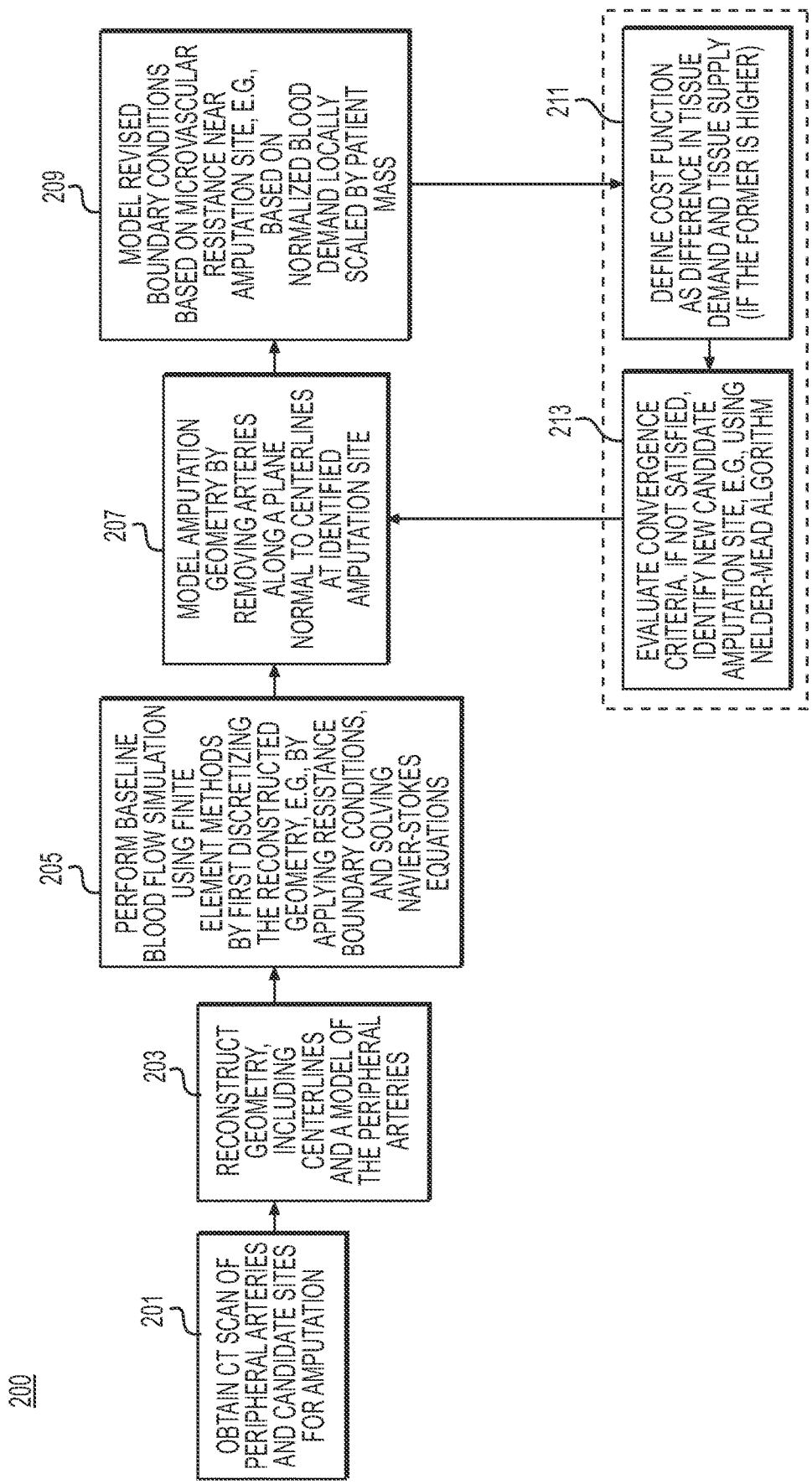
FIG. 2 is a block diagram of an exemplary method of simulating occluded arteries and/or optimizing occlusion-based treatments, according to an exemplary embodiment of the present disclosure.
Figure 3A:
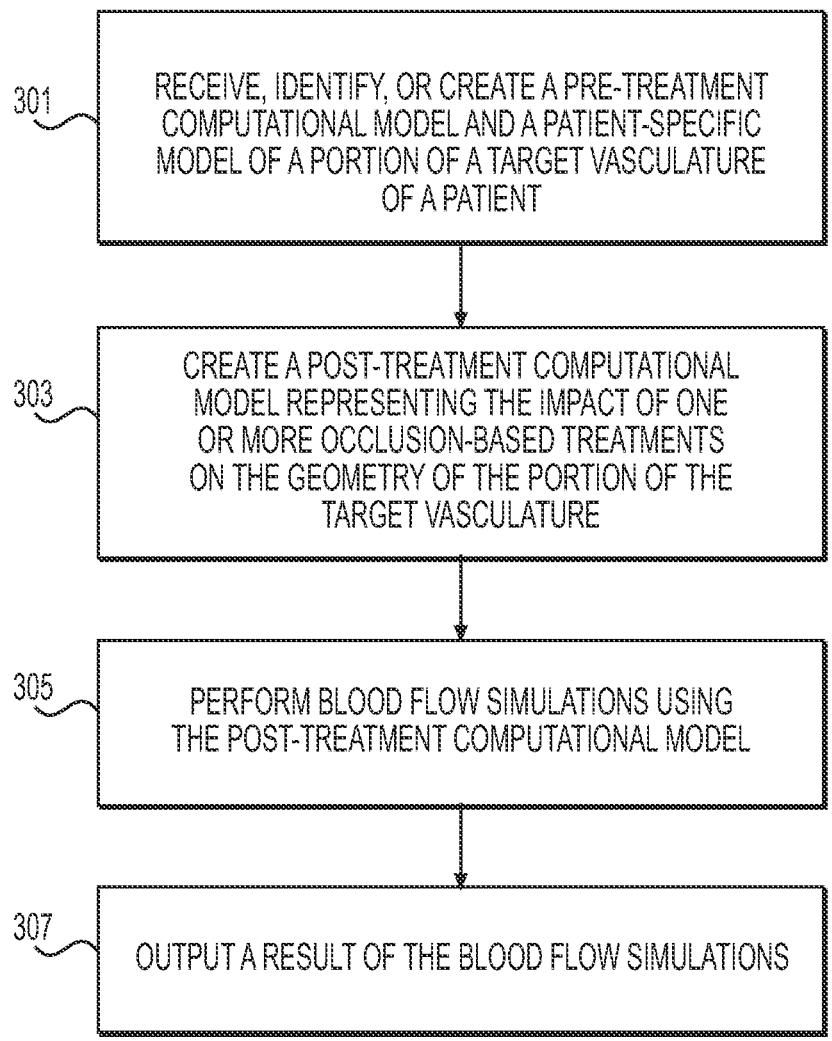
FIG. 3A is a block diagram of an exemplary method of simulating occluded arteries, according to an exemplary embodiment of the present disclosure.
Figure 3B:
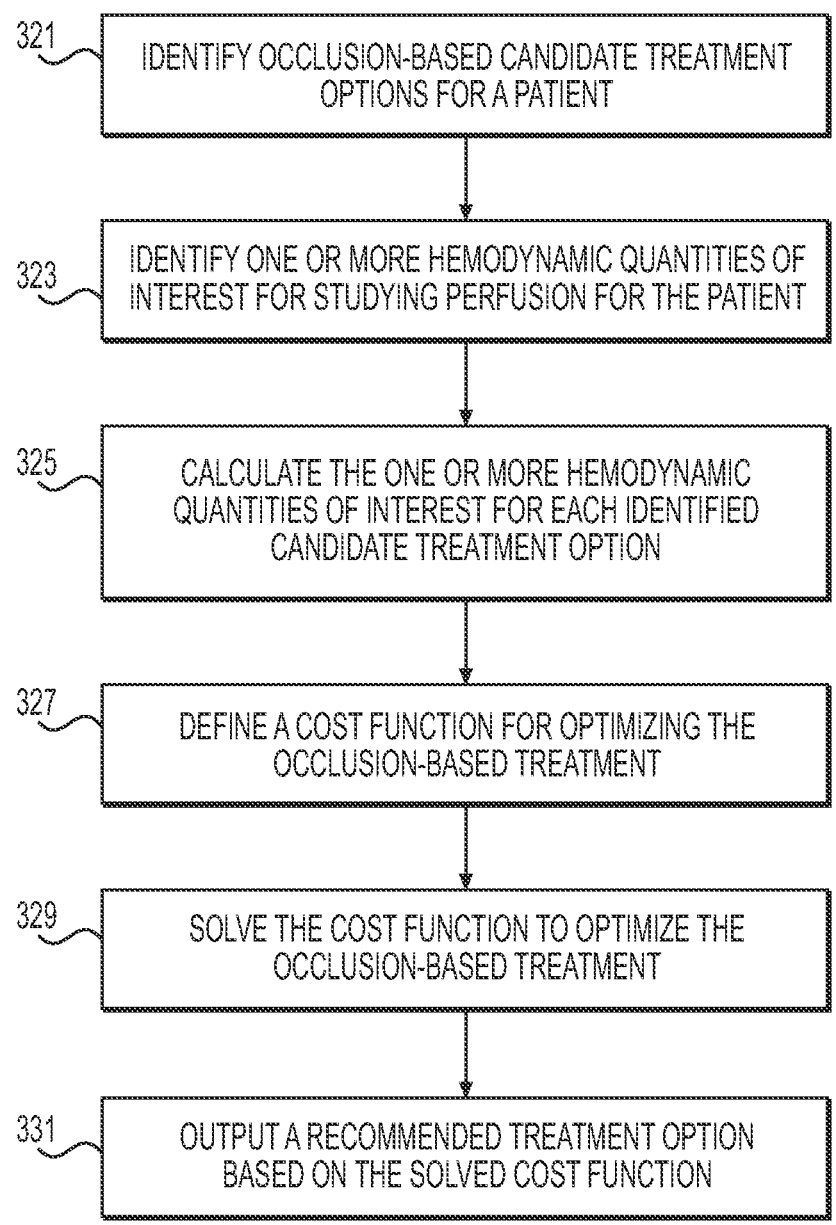
FIG. 3B is a block diagram of an exemplary method of optimizing occlusion-based treatments, according to an exemplary embodiment of the present disclosure.

Briefly, FIG. 2 depicts a schematic of a method for simulating occluded arteries and optimizing occlusion-based treatments. FIG. 3A depicts a flowchart for simulating occluded arteries and FIG. 3B depicts a flowchart for optimizing occlusion-based treatments in the occluded arteries simulated in the method of FIG. 3A. FIGS. 4A-6 depict flowcharts for specific embodiments of the methods of FIGS. 3A and 3B. For example, FIGS. 4A, 5A, and 6 each depict flowcharts for simulating occluded arteries for a respective particular treatment. FIGS. 4B and 5B depict flowcharts for optimizing respective treatments. Portions of each of the methods depicted in any of the flowcharts may be combined and/or interchanged with steps of other exemplary methods depicted in the flowcharts.

Specifically, FIG. 2 is a block diagram of an exemplary method 200 of simulating occluded arteries and optimizing occlusion-based treatments, according to an exemplary embodiment. In one embodiment, method 200 may include steps 201-209 to simulate occluded arteries, for instance, due to amputation. Steps 211 and 213 of method 200 may be directed toward optionally optimizing treatment, using the simulations performed in steps 201-209.

In one embodiment, step 201 may include obtaining a computerized tomography (CT) scan comprising peripheral arteries of a patient. Step 201 may further include obtaining candidate sites of the peripheral arteries (e.g., for amputation). In one embodiment, step 203 may include reconstructing a model of the patient's peripheral arteries, for instance, by producing a reconstruction of centerlines. Step 205 may include performing a baseline blood flow simulation using the reconstruction. For instance, performing the simulation of step 205 may include using a computational model including finite element methods. In one such case, the finite element methods may include discretizing the reconstructed geometry, applying resistance boundary conditions, and solving Navier-Stokes equations. The simulation of step 205 may provide estimates of pre-treatment hemodynamic characteristics.

Step 207 may include modeling post-surgery (e.g., amputation) geometry, for example, by removing arteries along a plane normal to centerlines (e.g., from the reconstructed model of step 203) at one or more of the identified candidate amputation sites. In one embodiment, step 209 may include modeling the revised boundary conditions (e.g., based on microvascular resistance near the amputation site). In one embodiment, resistances may be calculated based on normalized blood demand that is locally scaled by patient mass.

To optimize the treatments, one or both of steps 211 and 213 may optionally be performed. Specifically, step 211 may include defining a cost function for determining an optimal occlusion-based treatment. For instance, a cost function may be defined as a difference in tissue demand and tissue supply, with an optimization goal of providing tissue supply that exceeds tissue demand. The optimization goal may be a convergence criteria, depending on the cost function defined. Step 213 may include evaluating or solving the cost function for each of the candidate amputation sites (e.g., from step 201) and comparing each of the results against the convergence criteria. In one embodiment, step 213 may include generating a treatment recommendation (e.g., an amputation site) based on a comparison of the evaluated candidate amputation sites. In one embodiment, if the convergence criteria is not satisfied, step 213 may include identifying a new candidate amputation site (e.g., using a Nelder-Mead algorithm).

FIG. 3A is a block diagram of an exemplary method 300 of simulating occluded arteries, according to an exemplary embodiment. The method of FIG. 3A may be performed by server systems 106, based on information, images, and data received from physicians 102 and/or third party providers 104 over electronic network 101.

In one embodiment, step 301 may include acquiring a patient-specific model of at least a portion of the target vasculature of a patient. For example, the patient-specific model may include a digital representation encompassing an anatomical or other bodily system that is to be studied. The representation may include an image-based representation, measured variables, a list or table of parameter values and features representative of the anatomic or physiologic system, or a combination of the above. The representation may be assembled from image scans, e.g., CT, magnetic resonance imaging (MRI), ultrasound, etc. In one embodiment, the representation may be saved using digital storage, e.g., hard drive, network drive of a computer, laptop, server, or USB etc. Any treatment-specific parameters may also be received as input(s) to the patient-specific model. For example, treatment-specific parameters may include a dosage of radiation therapy associated with a cancer treatment. The dosage may be useful for ensuring or improving accuracy in modeling the effects of the cancer treatment. In modeling an occlusion-based treatment involving, for instance, amputation treatment planning may be enhanced by receiving information on treatment-specific parameters, including a candidate location of the amputation and/or the age of the patient receiving the amputation. Step 301 may further include receiving, identifying, or creating a computational model from the patient-specific model of the target vasculature. This computational model may serve as a pre-treatment computational model.

In one embodiment, step 301 may also include isolating a system of interest, e.g., by delineating the geometry, system properties, and specific conditions of the patient to study. Isolating the system of interest may include additional steps, e.g., image processing and reconstructing the system from a received raw image (e.g., the acquired digital representation).

In one embodiment, step 303 may include modeling the impact of one or more occlusion-based treatments on reconstructed geometry (e.g., reconstructions from step 301 including the system of interest). For example, step 303 may include identifying vessels of the reconstructed model (e.g., the previously described patient-specific model of 301) that may be occluded due to treatment and modifying the reconstructed model to create a post-treatment reconstructed model. For example, removal of blood vessels may be modeled or performed using Boolean operations on the reconstructed model. In removing the hypothetically occluded parts from the reconstructed model, additional outlet surfaces may be created. Step 303 may include further include generating a post-treatment computational model reflecting the occlusions. Parts of the computational model that are occluded may correspond to portions of the reconstructed geometry that are removed to create the post-treatment reconstructed model.

In one embodiment, step 305 may include analyzing flow re-distribution, boundary condition re-calibration, and hemodynamic impact of occlusion, using the computational model and acquired reconstructed model. For instance, blood flow simulations may be performed using the pre-treatment computational model created in step 301, e.g., by solving 3D Navier-Stokes equations, reduced order models, or via machine learning methods. Boundary conditions may be prescribed based on the application and system of interest. Additional aspects of defining boundary conditions may be provided with respect to specific embodiments described further in FIGS. 4A-6.

The blood flow simulations may further include modeling post-treatment changes in flow demand to micro-circulation territory. The change in flow demand to microcirculation territory may occur at the newly created outlet surfaces identified at step 303. In one embodiment, step 305 may include modeling the change in flow demand by altering boundary condition resistance in the post-treatment computational model in a way that may reflect microcirculatory resistance (or organ demand) at the site of occlusion. Step 305 may further include performing simulations of post-treatment systems of interest to compute the changes in organ perfusion, blood pressure, and other hemodynamic quantities of interest that may be caused by treatment. Boundary conditions may be kept constant if treatment primarily impacts distal vessels near outlets.

In one embodiment, step 307 may include outputting simulation results pre- and post-treatment. For example, step 307 may include creating a visual presentation, e.g., including graphical and/or pictorial comparisons or simulations for one or more treatments. The visual presentation or output may be included in a report to a health professional, e.g., transmitted over electronic network 101. Step 307 may also include outputting the simulation results for storage in an electronic storage medium.

FIG. 3B is a block diagram of an exemplary method 320 of optimizing occlusion-based treatments, according to an exemplary embodiment. The method of FIG. 3B may be performed by server systems 106, based on information, images, and data received from physicians 102 and/or third party providers 104 over electronic network 101. Method 320 includes optimizing treatment planning by optimizing treatment parameters.

In one embodiment, step 321 may include identifying candidate treatment options for a patient. Candidate treatment options may include commercially available occlusion-based treatment techniques and methods and/or occlusion-based treatments available to the particular patient. In one embodiment, step 323 may include identifying one or more hemodynamic quantities of interest to study. For example, one hemodynamic quantity of interest may include studying perfusion downstream of a treatment site.

Step 325 may include calculating the one or more hemodynamic quantities of interest for one or more of the identified candidate treatment options. In one embodiment, optimal occlusion-based therapy may including providing minimal blood flow in vascular regions identified to be occluded from circulation, while simultaneously ensuring healthy perfusion in other regions.

In one embodiment, step 327 may include defining a cost function for optimizing occlusion-based treatment. For example, a cost function may combine (i) blood flow in the occlusion zone, (ii) tissue perfusion in newly created outlet vessels, and/or (iii) tissue perfusion in other organs upstream of treatment location. A cost function may be defined as a difference between these values and a target value, either for each value or a combined value. In one embodiment, step 327 may further include defining one or more target values. For example, a target value for blood flow in an occlusion zone may be zero, and a target value for tissue perfusion may be the tissue perfusion demand of a healthy organ, based on patient mass (e.g., a value capped to zero if blood supply exceeds demand).

In one embodiment, step 329 may include solving the cost function. In other words, step 329 may include minimizing the cost function to optimize treatment planning. Step 329 may involve using an optimization method. For example, optimization methods may be generally classified as (i) derivative-free methods, (ii) gradient-based methods, or (iii) global optimization methods. Exemplary derivative-free methods may include repeating the evaluation of step 305 (from method 300) for different candidate treatments. Such methods may be used to find the optima (e.g. using a pattern search, Nelder-Mead, etc.). Exemplary gradient-based methods may include: steepest descent, conjugate-gradient, Broyden-Fletcher-Goldfarb-Shanno (BFGS), solving an adjoint equation, or linearizing and deriving parameter sensitivity equations for the Navier-Stokes equations. In some cases, a BFGS may be based on a gradient of blood pressure and velocity to parameters calculated using methods (e.g., finite difference). Exemplary global optimization methods may include evolutionary search or genetic algorithms.

In one embodiment, step 331 may include outputting a recommended treatment option, based on the optimization method calculations. In some embodiments, step 331 may include generating one or more renderings of the recommended treatment options and/or renderings comparing one or more treatment options. For instance, the renderings may include graphical or pictorial, interactive user interfaces, including displays on or comparing hemodynamic impact of one or more of the treatment options.

Figure 4A:
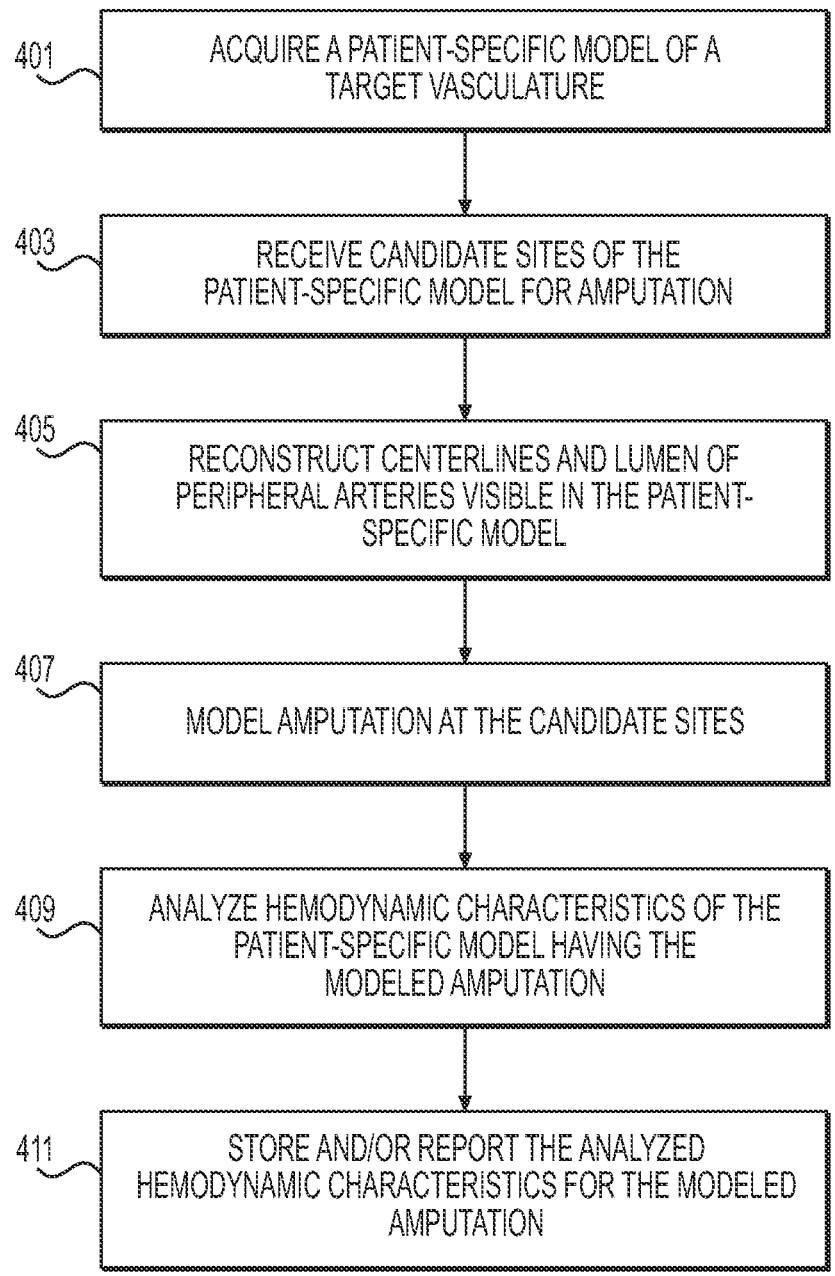
FIG. 4A is a block diagram of an exemplary method of modeling hemodynamic impact of amputation, according to an exemplary embodiment of the present disclosure.
Figure 4B:
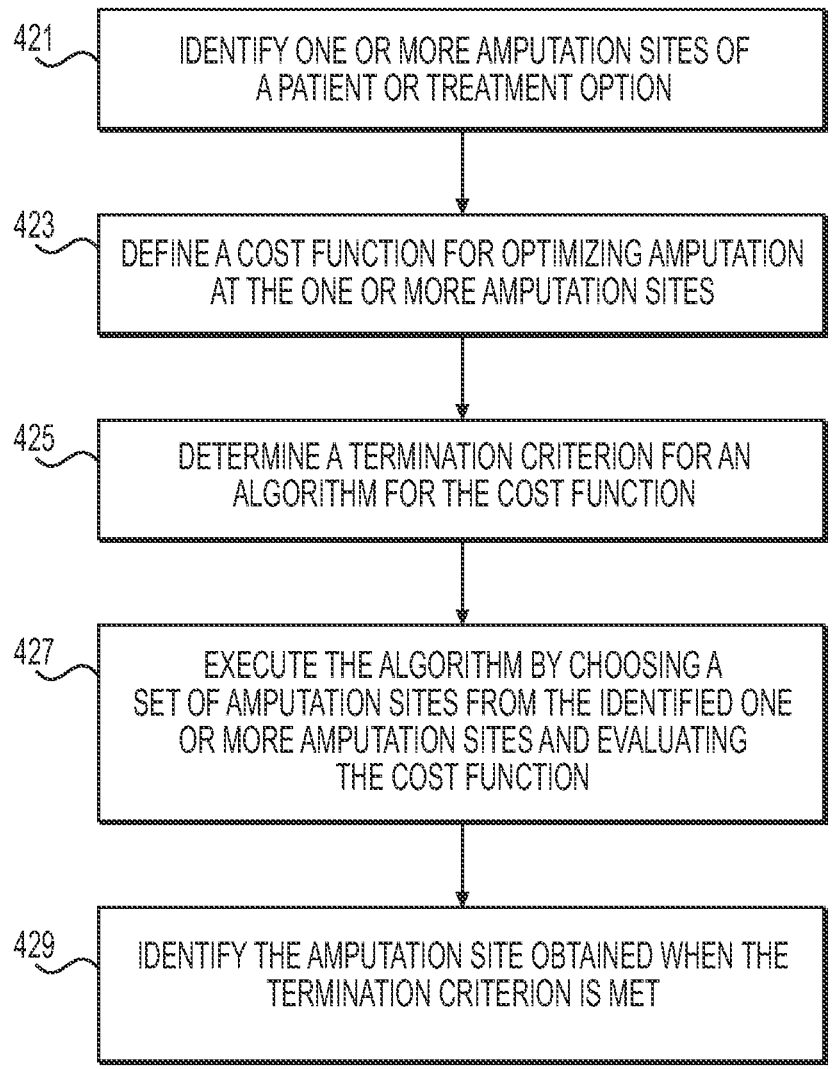
FIG. 4B is an exemplary method of optimizing the location at which the amputation is performed, according to an exemplary embodiment of the present disclosure.

FIG. 4A is a block diagram of an exemplary method 400 of modeling hemodynamic impact of amputation (e.g., of a leg or arm), according to an exemplary embodiment. FIG. 4B is a block diagram of an exemplary method 420 of optimizing the location at which the amputation is performed, according to an exemplary embodiment. The methods of FIGS. 4A and 4B may be performed by server systems 106, based on information, images, and data received from physicians 102 and/or third party providers 104 over electronic network 101.

Amputation may involve surgical removal of a limb. This type of surgery may be important and frequently performed, especially amongst geriatric patients. Peripheral artery disease may be one reason for amputation. For instance, vessel lumen narrowing may cause poor circulation in the lower limbs, which may result in dead tissue, and possibly, infection. The goal of the surgery may include amputating high enough on a limb so as to minimize risk of re-infection and gangrene. However, the higher the amputation zone, the greater the loss of functionality may be. A higher amputation zone may translate into greater loss of mobility and the need for longer post-operative care. Hence, an optimal amputation may be just high enough on a patient's extremity to minimize risk of gangrene and yet ensure healthy tissue perfusion post-surgery. Current surgical practice may identify amputation zones using physician experience and accepted clinical practice, without accounting for healing response (which may be patient-specific).

The following sites may be candidates for certain leg amputation sites-(a) transfemoral (above knee), (b) through knee, (c) transtibial (below knee), (d) ankle, and (e) transmetatarsal. Studies suggest that two strong predictors of amputation site may include flow rate and pressure (e.g., to ensure a sufficient skin capillary flow level). For example, trans-tibial amputations may heal in patients with popliteal systolic pressures of more than 70 mm Hg. In comparing the pressure at a proposed amputation site to the pressure of a brachial artery, a ratio of more than 0.35 may be adequate for healing in a non-diabetic, while a ratio of 0.45 may be adequate for a diabetic. A predictor of amputation success may include using Doppler ultrasonography to measure arterial blood pressure at the proposed amputation site. Non-invasive techniques of blood flow simulation for determining the lowest level of successful limb amputation may be a valuable aid to clinical judgment.

Method 400 of FIG. 4A may be used to model the hemodynamic impact of limb amputation at a first amputation site, and compare the impact at the first amputation site against the hemodynamic impact corresponding to amputation at another amputation site. Several amputation sites may be compared in order to provide effective treatment while allowing a patient to maintain as much of a limb as possible. In doing so, method 400 may further provide an optimal location of amputation.

In one embodiment, step 401 may include acquiring a patient-specific model of target vasculature in a patient's anatomy. For example, step 401 may include acquiring a digital representation encompassing, for instance, the entire arterial system of the patient's limb, including candidate locations of amputation. Step 401 may further include receiving input data, e.g., image-based representation(s), measured variables (e.g., blood pressure and patient body mass/height), etc.

In one embodiment, step 403 may include receiving candidate locations for amputation as input, e.g., from a database or physician. Image data may be received in the form of CT, MRI, ultrasound etc. This input may be saved using digital storage, e.g., hard drive, network drive of a computer, laptop, server, USB, etc.

In one embodiment, step 403 may also include receiving input variables for optimization of amputation location. These variables may include parameters for the cost function, e.g., desired tissue perfusion value, desired blood pressure and the weighting of different cost functions. The variables may further include infeasible locations for surgery (e.g., locations downstream of the most proximal gangrene location) and/or radius around each infeasible location. In other words, receiving the infeasible locations for surgery may help speed the optimization calculations by focusing the calculations on feasible amputation locations.

In one embodiment, step 405 may include reconstructing the centerlines and lumen of each peripheral artery visible in patient-specific model (e.g., the data in step 401). For instance, step 405 may include using a one or both of automatic and manual segmentation algorithms.

In one embodiment, step 407 may include modeling amputation at the candidate sites (received in step 401). In one embodiment, amputation at the identified candidate sites (e.g., in step 405) may be modeled by generating a simulation model with arteries removed downstream of a plane perpendicular to centerlines at the location of amputation. The modeled amputation site may be treated as the new boundaries of the simulation model.

In one embodiment, step 409 may include analyzing, for instance, flow re-distribution, boundary condition re-calibration, and/or hemodynamic impact of amputation. Flow demand to the micro-circulation region may depend on the location of amputation, as well as limb mass, e.g., flow demand may be scaled based on scaling laws applied to scaling nominal demand by the patient's limb mass. In one embodiment, analyzing flow re-distribution or demand may include building a computational model (e.g., a finite element model) of the patient pre- and post-amputation, and custom boundary conditions at different regions of the model may be used to calculate blood flow variables pre- and post-amputation. Since new outlet surfaces in the computational model may be formed post-amputation, step 409 may further include defining new boundary conditions based on microcirculatory demand at location of amputation.

In one embodiment, step 411 may include storing and/or reporting differences in hemodynamics (e.g., perfusion level and blood pressure) at a site of amputation pre- and post-surgery. In some cases, a physician or health care provider may directly receive the analysis or output from step 411.

FIG. 4B depicts a block diagram of exemplary method 420 for further leveraging simulations, e.g., by calculating an optimal site location. In one embodiment, step 421 may include identifying feasible and/or infeasible amputation sites of a patient or a particular treatment option. For example, step 421 may be similar to step 403 in receiving data regarding amputation locations. In one embodiment, input from step 403 may also provide feasible options for amputation for step 421. Any amputation location not feasible (e.g., due to constraints in the operation room) may also be received as input in steps 403 or 421.

In one embodiment, step 423 may include defining a cost function for optimizing an amputation site, e.g., a weighted sum of (i) normalized signed difference between desired and computed blood pressure and (ii) normalized mean absolute difference between desired and computed tissue perfusion level. In one embodiment, the weights for the two terms may be input by a user (e.g., a physician) and/or calculated or obtained from a database. As previously stated, each of the terms of the cost function may be normalized. The cost function may be a general cost function for optimizing amputation sites, or a cost function specific to the patient associated with the patient-specific model (e.g., of step 401).

In one embodiment, step 425 may include determining an algorithm termination criterion. Determining an algorithm termination criterion may involve determining a desired hemodynamic value. This determination may include calculating a desired hemodynamic value (e.g., based on population-averaged healthy value at an amputation site) or receiving a desired hemodynamic value, e.g., as input by a physician or health care profession.

In one embodiment, step 427 may include executing an optimization algorithm by choosing an initial random set of amputation sites (e.g., from the input at step 425) and evaluating the cost function (e.g., the cost function defined at step 423). In one embodiment, step 427 may include using the Nelder-Mead algorithm to identify new candidate amputation sites based on the evaluated points, and construct a simplex with existing points as vertices. Amputation sites in the proximity of infeasible surgical geometries may be given a very high cost function value (e.g., infinity). In one embodiment, step 427 may be performed until the optimization algorithm termination criterion is met.

In one embodiment, step 429 may include identifying the amputation site obtained when an optimization algorithm termination criterion is met, and designating the amputation side as the optimal site. Step 429 may further include storing and/or outputting the optimal site, e.g., to an electronic storage medium accessible by one or more users.

Figure 5A:
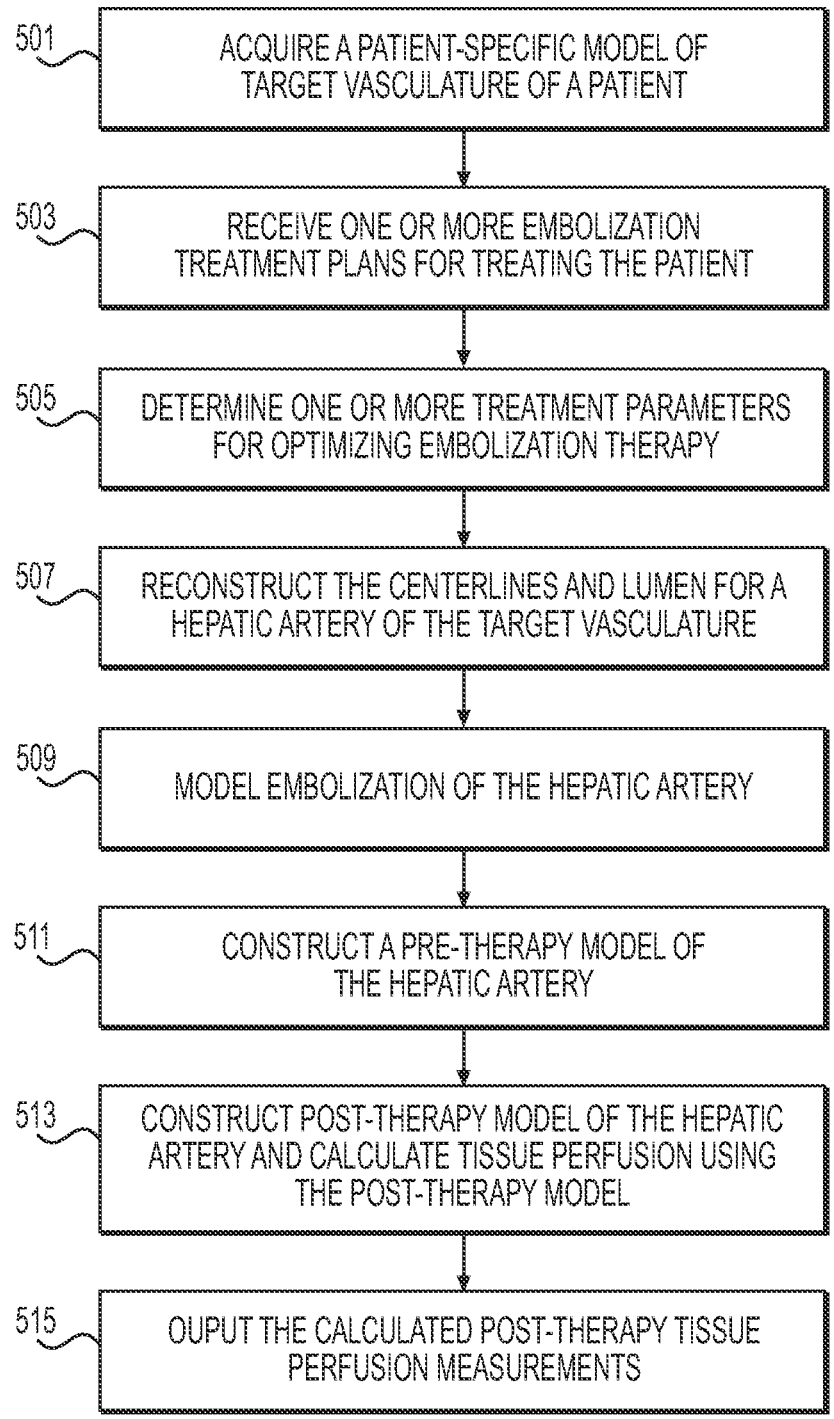
FIG. 5A is a block diagram of an exemplary method of simulating embolization therapy of the liver, according to an exemplary embodiment of the present disclosure.
Figure 5B:
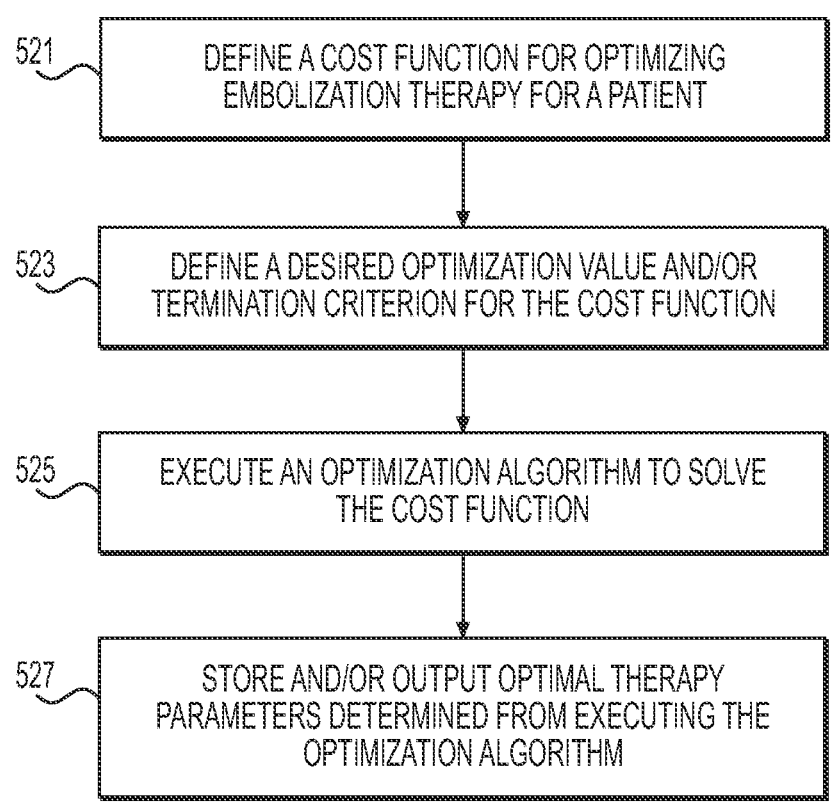
FIG. 5B is a block diagram of an exemplary method of optimizing embolization therapy, according to an exemplary embodiment of the present disclosure.

FIG. 5A is a block diagram of an exemplary method 500 of simulating embolization therapy for the liver (e.g., in a scenario involving liver cancer), according to an exemplary embodiment. FIG. 5B is a block diagram of an exemplary method 520 of optimizing embolization therapy, according to an exemplary embodiment. The methods of FIGS. 5A and 5B may be performed by server systems 106, based on information, images, and data received from physicians 102 and/or third party providers 104 over electronic network 101.

Cancer cells in the liver may be fed by the hepatic artery, while normal cells may be fed by the portal vein. Embolization of a patient's hepatic artery may impact the patient's liver perfusion, as well as perfusion of downstream arteries. An extent of radiation therapy may be computed through simulations. The goal of successful embolization may be to isolate cancer cells from circulation, while simultaneously ensuring sufficient tissue perfusion. The embodiment below may also be used for embolization of other types of cancers, e.g., bile duct cancer, gall bladder cancer, or even cerebral embolization to treat aneurysms in the brain.

In one embodiment, step 501 may include acquiring a patient-specific model of the target vasculature of a patient. For example, step 501 may include acquiring a digital representation encompassing, for instance, a patient's hepatic artery, a portion of a patient's aorta that the hepatic artery branches off of, and/or other downstream vessels of interest. Step 501 may further include receiving inputs including patient organ volume and/or mass to account for changes in blood flow demand, e.g., due to changes in organ mass. The liver and various organs that may be included in the simulation may undergo tissue reduction/destruction and/or regeneration. For instance, treatment for liver cancer may involve removing a portion of a liver, causing a reduction in liver mass. Heart attacks also often damage muscle cells of the heart and lead to a reduction of heart mass and flow demand. An artery may remodel over time to reflect the amount of blood it carries, given its associated organ mass. Inputting patient organ volume and/or mass may allow computations to account for scaling loss, a reduced need for blood flow through afferent (upstream) arter(ies) feeding a diminished organ mass. In addition, organs may also regenerate and progressively increase in mass. For example, an organ may regenerate in response to treatment or recovery. The reduction in an afferent artery in such a case may be transitory. The patient organ volume and/or mass input may provide for changes in flow demand that may be associated with fluctuations in organ volume and/or mass.

In one embodiment, step 503 may include determining whether various treatment plans are available (either commercially and/or for the patient). If so, step 503 may further include receiving one or more treatment plans (e.g., arterial embolization, chemoembolization, and radio-embolization) as inputs. The extent of therapy (e.g., radiation dose if using radio-embolization) may also be received as an input.

In one embodiment, step 505 may include determining a range of treatment parameters, e.g., parameters for optimizing embolization therapy. In one embodiment, step 505 may also include specifying an embolization location. Method 500 may further include step 507 of reconstructing the centerlines and lumen for a hepatic artery or hepatic arteries (e.g., common hepatic, left and right hepatic), the portion of aorta visible and other arteries visible in the CT scan (e.g., mesenteric) using a combination of automatic and manual segmentation algorithms.

In one embodiment, step 509 may include modeling embolization of the hepatic arter (ies). Depending on the type of therapy (e.g., arterial embolization, chemoembolization or radio-embolization), an embolization region may be either directly available (e.g., from former knowledge on the patient) or the length and location of embolization may be modeled based on radiation dose. In one embodiment, the length of an embolized region may be modeled as proportional to the radiation dose unless otherwise specified.

In one embodiment, steps 511 and 513 may include analyzing flow re-distribution and hemodynamic impact of embolization therapy for the patient. For example, step 511 may include constructing a pre-therapy model. For instance, step 511 may include constructing a finite element mesh of the reconstructed patient-specific model (e.g., from step 507). The pre-therapy level of tissue perfusion for the liver may also be calculated, as well as perfusion levels of other organs upstream of the therapy, e.g., the gall bladder, pancreas etc.

Step 513 may include constructing a post-therapy patient-specific model, e.g., a new finite element mesh of the embolized hepatic artery. Step 513 may further include calculating tissue perfusion in the patient's liver post-therapy for the candidate therapies (e.g., from step 503). In one embodiment, step 515 may include storing and/or outputting post-therapy tissue perfusion measurements, e.g., to an electronic storage medium for retrieval by a physician. The output for step 515 may further include difference in tissue perfusions for other organs pre-therapy and post-therapy.

FIG. 5B is a block diagram of exemplary method 520 for optimizing embolization therapy. In one embodiment, step 521 may include defining a cost function for optimizing embolization therapy for a patient. For instance, step 521 may include defining a cost function based on a difference in tissue perfusion pre- and post-therapy. Since blood supply to healthy cells in the liver may be fed by portal vein and arteries other than the hepatic artery, the difference in net liver perfusion may serve as a cost function. Perfusion of other organs may change as a result of the embolization, hence deviation from desired perfusion levels in these organs may also be added to the cost function. Each term in the optimization may be treated with equal weight, unless inputs dictate otherwise (e.g., in step 503).

In one embodiment, step 523 may include defining organ perfusion pre-therapy as a desired optimization value and/or termination criterion. In one embodiment, step 525 may include executing an optimization algorithm to solve the cost function. For example, step 525 may include employing the Nelder-Mead algorithm to identify an optimal therapy, for instance, a therapy that minimizes the cost function. Step 525 may include selecting an initial set of parameters (e.g., dosage) at random. Subsequently, at each step in the Nelder-Mead algorithm, a new parameter may be identified by constructing simplexes using existing points and choosing an operation between reflection, reduction, contraction, or reduction. By successively performing this step, optimal therapy parameters may be identified when the termination criterion is reached.

In one embodiment, step 527 may include storing and/or outputting the optimal therapy parameters, e.g., to an electronic storage medium. Step 527 may further include creating a rendering to present the optimal therapy parameters.

Figure 6:
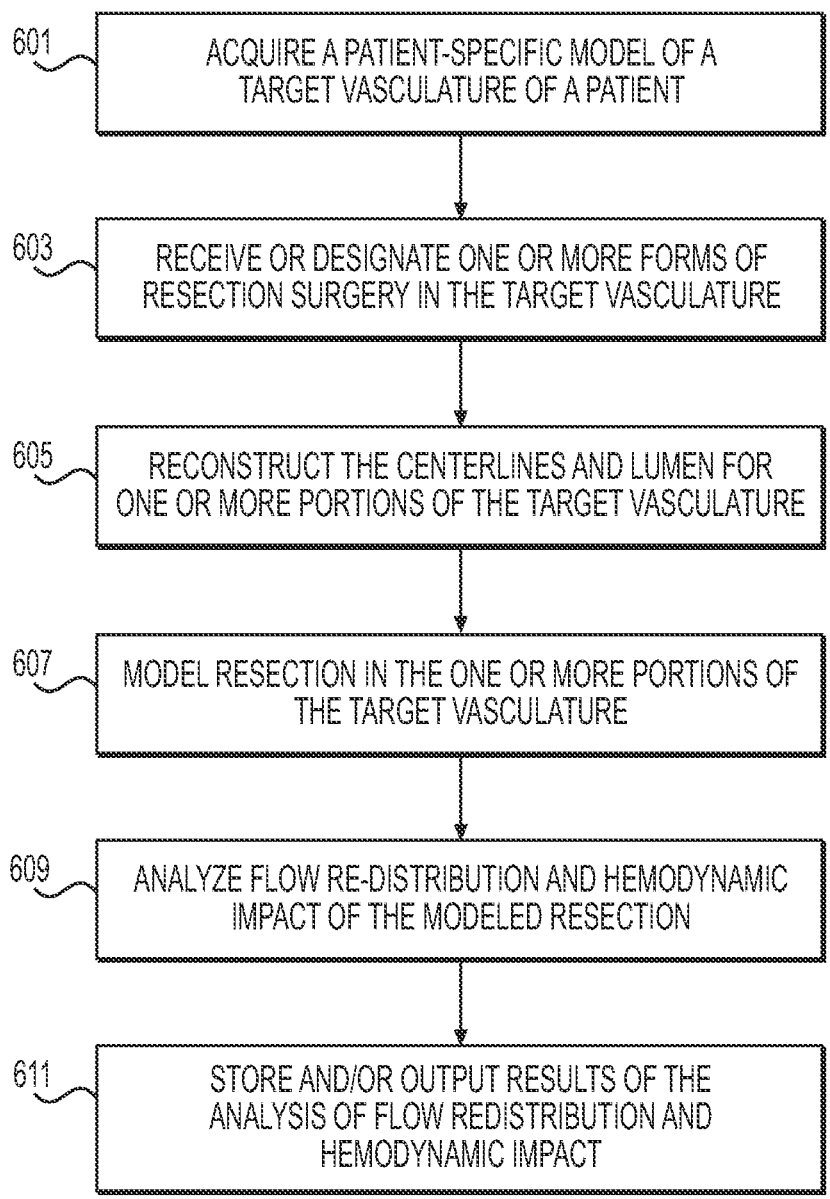
FIG. 6 is a block diagram of an exemplary method of simulating vascular resection, according to an exemplary embodiment of the present disclosure.

FIG. 6 is a block diagram of an exemplary method 600 of simulating vascular resection (e.g., for pancreaticoduodenectomy), according to an exemplary embodiment. The method of FIG. 6 may be performed by server systems 106, based on information, images, and data received from physicians 102 and/or third party providers 104 over electronic network 101.

Resection of the superior mesenteric artery or portal vein may be performed as an occlusion-based treatment when a tumor cannot be localized to organs and separated from surrounding arteries or veins. This may be followed by reconstruction of a portion of the original arterial system. Exemplary method 600 may also be used for surgical resection to remove abnormal tissue, including neurogenic, mediastinal, or germ cell tumors, or thymoma. Generally, this embodiment may also include cutting a portion of an organ if a tumor is localized, and the post-resected model may involve changing organ demand to reflect the resected geometry.

In one embodiment, step 601 may include acquiring a patient-specific model of a target vasculature. For example, step 601 may include acquiring a digital representation encompassing a patient's portal vein or superior mesenteric vein, a portion of the patient's aorta that the hepatic artery branches off of, and/or other downstream vessels of interest. Patient organ volume and/or mass may also serve as input for scaling loss to compute flow demand of pancreas and various organs that may be included in the simulation.

In one embodiment, step 603 may include receiving or designating one or more forms of resection surgery to simulate, e.g., tangential or segmental resection. For example, a user (e.g., a physician) may input one or more forms of resection surgery to study. These inputs may include candidate therapies (e.g., for a specific patient).

In one embodiment, step 605 may include reconstructing the centerlines and lumen for the received portal vein and superior mesenteric arteries, the portion of aorta visible, and/or other arteries visible in the CT scan (e.g., mesenteric). Step 605 may be performed using one or both of automatic and manual segmentation algorithms.

In one embodiment, step 607 may include modeling resection. For example, step 607 may include creating a post-resection computational model of the received or designated resection surgery (e.g., from step 603). If a tangential resection is preferred, a portion of the superior mesenteric artery or portal vein may be removed along a section of the wall parallel to centerlines. The lumen diameter may be correspondingly reduced based on an extent of resection. If a segmental resection may be preferred, a portion of the arteries in the reconstructed model (e.g., from step 605) may be removed. Step 607 may further include modeling additional patching, if performed post-resection. In one embodiment, resection or surgical repair of an artery that has undergone injury or having a portion of the vessel being removed, may result in stenosis or narrowing that may obstruct blood flow. In one embodiment, patching may include sewing a segment (e.g., a patch) of material to replace artery walls that are missing or damaged from surgery. Material used for patching may include an autogenous vein and/or prosthetic graft material. Patching an artery may increase its diameter (and cross-sectional area), thus correcting a stenosis that may otherwise obstruct blood flow.

In one embodiment, step 609 may include analyzing flow re-distribution and hemodynamic impact of the resection. For example, step 609 may include constructing a pre-resection finite element mesh of the reconstructed model (from step 605). Step 609 may further include calculating a level of tissue perfusion to the pancreas. Perfusion levels of other organs upstream of the therapy, e.g., the gallbladder, pancreas, etc. may also be calculated. Step 609 may also include constructing a finite element mesh of the resected artery. Tissue perfusion in the pancreas post-therapy may be calculated for one or more candidate therapies.

In one embodiment, step 611 may include storing and/or outputting results of the analysis from step 609, e.g., into an electronic storage medium accessible by a user/physician. The output for step 611 may further include differences in tissue perfusions for other organs, pre-resection versus post-resection.

The present disclosure may apply to modeling various occlusion-based treatments and/or selecting an occlusion-based treatment for a patient, based on the modeling. Modeling post-treatment resultant blood flow permits comparison of different treatments so that an optimal treatment may be selected for a particular patient.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of planning an occlusive procedure, the method comprising:
 obtaining image data of at least a portion of a patient's vasculature;

generating a patient-specific anatomic model of the portion of the patient's vasculature based on the image data by reconstructing at least one centerline and at least one corresponding lumen of at least one blood vessel of the patient's vasculature visible in the image data;

determining an initial computational model of blood flow through the patient's vasculature based on the patient-specific anatomic model, the initial computational model including a pre-treatment boundary condition;

determining a pre-treatment value for a blood flow characteristic by performing a calculation of blood flow using the initial computational model;

determining a patient-specific target value for the blood flow characteristic;

prior to treatment of the patient, obtaining one or more candidate sites for the occlusive procedure;

prior to treatment of the patient, and for each respective candidate site of the one or more candidate sites, performing a candidate site evaluation that includes:

determining a post-treatment boundary condition by modifying the patient-specific anatomic model to include one or more cross-sectional outlets, surfaces, or boundaries in modeled vasculature of the patient-specific anatomic model corresponding to an occlusion at the respective candidate site by removing a portion of the patient's vasculature from the patient-specific anatomical model that is downstream of a plane perpendicular to the at least one centerline at the respective candidate site;

updating the initial computational model based on the post-treatment boundary condition in the modified patient-specific anatomic model; and noninvasively determining a respective post-treatment value of the blood flow characteristic value by performing a calculation of blood flow using the updated computational model;

determining whether the respective post-treatment value of the blood flow characteristics meets or exceeds the patient-specific target value;

in response to determining that the respective post-treatment value does not meet the patient-specific target value, iteratively identifying a new candidate site and repeating the candidate site evaluation for the new candidate site until the respective post-treatment value of the blood flow characteristics meets or exceeds the target value; and in response to determining that the respective post-treatment value of the blood flow characteristics meets or exceeds the patient-specific target value, generating a plan for the occlusive procedure that includes a recommendation for selection of a treatment site corresponding to the respective post-treatment value.

2. The computer-implemented method of claim 1, wherein the calculation of blood flow includes Navier-Stokes equations, reduced order models, or machine learning methods.

3. The computer-implemented method of claim 1, wherein the post-treatment boundary condition is based on circulatory resistance or organ demand at a location of the patient's vasculature associated with the respective candidate site.

4. The computer-implemented method of claim 1, wherein the occlusive procedure includes an amputation, an embolization therapy, or a vascular resection.

5. The computer-implemented method of claim 1, further comprising:

determining one or more cross-sectional outlets, surfaces, or boundaries of the patient's vasculature created by stoppage of blood flow through the patient's vasculature or removal of a portion of the patient's vasculature at each respective candidate site, wherein the post-treatment boundary condition is a boundary condition of at least one of the determined one or more cross-sectional outlets, surfaces, or boundaries of the patient's vasculature.

6. The computer-implemented method of claim 1, wherein the blood flow characteristic includes organ perfusion or blood pressure.

7. The computer-implemented method of claim 1, wherein identifying the new candidate site includes using a Nelder-Mead algorithm.

8. The computer-implemented method of claim 1, wherein determining whether the respective post-treatment value of the blood flow characteristics meets or exceeds the patient-specific target value includes evaluating a cost function.

9. The computer-implemented method of claim 8, wherein:

the cost function is defined as a difference in tissue demand and tissue supply; and the target value is determined based on providing tissue supply that exceeds tissue demand for the patient.

10. A system for planning an occlusive procedure, comprising:

at least one memory storing instructions; and at least one processor operatively connected to the at least one memory, and configured to execute the instruction to perform operations including:

obtaining image data of at least a portion of a patient's vasculature;

generating a patient-specific anatomic model of the portion of the patient's vasculature based on the image data by reconstructing at least one centerline and at least one corresponding lumen of at least one blood vessel of the patient's vasculature visible in the image data;

determining an initial computational model of blood flow through the patient's vasculature based on the patient-specific anatomic model, the initial computational model including a pre-treatment boundary condition;

determining a pre-treatment value for a blood flow characteristic by performing a calculation of blood flow using the initial computational model;

determining a patient-specific target value for the blood flow characteristic;

prior to treatment of the patient, obtaining one or more candidate sites for the occlusive procedure;

prior to treatment of the patient, and for each respective candidate site of the one or more candidate sites, performing a candidate site evaluation that includes:

determining a post-treatment boundary condition by modifying the patient-specific anatomic model to include one or more cross-sectional outlets, surfaces, or boundaries in modeled vasculature of the patient-specific anatomic model corresponding to an occlusion at the respective candidate site by removing a portion of the patient's vasculature from the patient-specific anatomical model that is downstream of a plane perpendicular to the at least one centerline at the respective candidate site;

updating the initial computational model based on the post-treatment boundary condition in the modified patient-specific anatomic model; and noninvasively determining a respective post-treatment value of the blood flow characteristic value by performing a calculation of blood flow using the updated computational model;

determining whether the respective post-treatment value of the blood flow characteristics meets or exceeds the patient-specific target value;

in response to determining that the respective post-treatment value does not meet the patient-specific target value, iteratively identifying a new candidate site and repeating the candidate site evaluation for the new candidate site until the respective post-treatment value of the blood flow characteristics meets or exceeds the target value; and in response to determining that the respective post-treatment value of the blood flow characteristics meets or exceeds the patient-specific target value, generating a plan for the occlusive procedure that includes a recommendation for selection of a treatment site corresponding to the respective post-treatment value.

11. The system of claim 10, wherein the calculation of blood flow includes Navier-Stokes equations, reduced order models, or machine learning methods.

12. The system of claim 10, wherein the post-treatment boundary condition is based on circulatory resistance or organ demand at a location of the patient's vasculature associated with the respective candidate site.

13. The system of claim 10, wherein the occlusive procedure includes an amputation, an embolization therapy, or a vascular resection.

14. The system of claim 10, wherein:
the operations further include determining one or more cross-sectional outlets, surfaces, or boundaries of the patient's vasculature created by stoppage of blood flow through the patient's vasculature or removal of a portion of the patient's vasculature at each respective candidate site; and
the post-treatment boundary condition is a boundary condition of at least one of the determined one or more cross-sectional outlets, surfaces, or boundaries of the patient's vasculature.

15. The system of claim 10, wherein the blood flow characteristic includes organ perfusion or blood pressure.

16. The system of claim 10, wherein identifying the new candidate site includes using a Nelder-Mead algorithm.

17. The system of claim 10, wherein:
determining whether the respective post-treatment value of the blood flow characteristics meets or exceeds the patient-specific target value includes evaluating a cost function;
the cost function is defined as a difference in tissue demand and tissue supply; and
the target value is determined based on providing tissue supply that exceeds tissue demand for the patient.

18. A non-transitory computer-readable medium comprising instructions that are executable by a processor to perform operations including:
obtaining image data of at least a portion of a patient's vasculature;
generating a patient-specific anatomic model of the portion of the patient's vasculature based on the image data by reconstructing at least one centerline and at least one corresponding lumen of at least one blood vessel of the patient's vasculature visible in the image data;
determining an initial computational model of blood flow through the patient's vasculature based on the patient-specific anatomic model, the initial computational model including a pre-treatment boundary condition;
determining a pre-treatment value for a blood flow characteristic by performing a calculation of blood flow using the initial computational model;
determining a patient-specific target value for the blood flow characteristic;
prior to treatment of the patient, obtaining one or more candidate sites for the occlusive procedure;
prior to treatment of the patient, and for each respective candidate site of the one or more candidate sites, performing a candidate site evaluation that includes:
determining a post-treatment boundary condition by modifying the patient-specific anatomic model to include one or more cross-sectional outlets, surfaces, or boundaries in modeled vasculature of the patient-specific anatomic model corresponding to an occlusion at the respective candidate site by removing a portion of the patient's vasculature from the patient-specific anatomical model that is downstream of a plane perpendicular to the at least one centerline at the respective candidate site;
updating the initial computational model based on the post-treatment boundary condition in the modified patient-specific anatomic model; and
noninvasively determining a respective post-treatment value of the blood flow characteristic value by performing a calculation of blood flow using the updated computational model;
determining whether the respective post-treatment value of the blood flow characteristics meets or exceeds the patient-specific target value;
in response to determining that the respective post-treatment value does not meet the patient-specific target value, iteratively identifying a new candidate site and repeating the candidate site evaluation for the new candidate site until the respective post-treatment value of the blood flow characteristics meets or exceeds the target value; and
in response to determining that the respective post-treatment value of the blood flow characteristics meets or exceeds the patient-specific target value, generating a plan for the occlusive procedure that includes a recommendation for selection of a treatment site corresponding to the respective post-treatment value.

19. The non-transitory computer-readable medium of claim 18, wherein:
the operations further include determining one or more cross-sectional outlets, surfaces, or boundaries of the patient's vasculature created by stoppage of blood flow through the patient's vasculature or removal of a portion of the patient's vasculature at each respective candidate site; and
the post-treatment boundary condition is a boundary condition of at least one of the determined one or more cross-sectional outlets, surfaces, or boundaries of the patient's vasculature.

20. The non-transitory computer-readable medium of claim 18, wherein:

determining whether the respective post-treatment value of the blood flow characteristics meets or exceeds the patient-specific target value includes evaluating a cost function;

the cost function is defined as a difference in tissue demand and tissue supply; and the target value is determined based on providing tissue supply that exceeds tissue demand for the patient.

\* \* \* \* \*